United States Patent
Hofmann et al.

(10) Patent No.: US 7,801,965 B2
(45) Date of Patent: Sep. 21, 2010

(54) METHOD AND APPARATUS FOR PROCESSING DATA, AND MEDICAL APPLIANCE SYSTEM FOR PROCESSING DATA

(75) Inventors: Ralf Hofmann, Nuremberg (DE); Ivan Murphy, Baiersdorf (DE); Andreas Schuelke, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 1266 days.

(21) Appl. No.: 11/093,239

(22) Filed: Mar. 30, 2005

(65) Prior Publication Data

US 2005/0234325 A1    Oct. 20, 2005

Related U.S. Application Data

(60) Provisional application No. 60/557,689, filed on Mar. 31, 2004.

(30) Foreign Application Priority Data

Mar. 31, 2004    (DE)    ........................ 10 2004 016 578

(51) Int. Cl.
| | |
|---|---|
| G06F 15/16 | (2006.01) |
| G06F 15/167 | (2006.01) |
| G06F 7/00 | (2006.01) |
| A61B 5/05 | (2006.01) |

(52) U.S. Cl. .................. 709/211; 709/213; 709/248; 707/610; 600/408; 600/410

(58) Field of Classification Search .................. 709/211, 709/248, 213; 600/408, 410; 705/2; 707/610
See application file for complete search history.

(56) References Cited

U.S. PATENT DOCUMENTS

| | | | | |
|---|---|---|---|---|
| 5,513,101 | A | * | 4/1996 | Pinsky et al. .................... 705/3 |
| 5,668,998 | A | * | 9/1997 | Mason et al. ................ 717/104 |
| 5,971,923 | A | * | 10/1999 | Finger ......................... 600/437 |
| 5,991,760 | A | | 11/1999 | Gauvin et al. |
| 6,260,021 | B1 | * | 7/2001 | Wong et al. ..................... 705/2 |
| 2002/0016718 | A1 | * | 2/2002 | Rothschild et al. ............. 705/2 |
| 2002/0023172 | A1 | * | 2/2002 | Gendron et al. ............. 709/238 |
| 2002/0131625 | A1 | * | 9/2002 | Vining et al. ................ 382/128 |
| 2004/0083257 | A1 | | 4/2004 | Gortler et al. |
| 2004/0122790 | A1 | * | 6/2004 | Walker et al. .................. 707/1 |

FOREIGN PATENT DOCUMENTS

DE    10230878 A1    2/2004

* cited by examiner

*Primary Examiner*—Ranodhi N Serrao
(74) *Attorney, Agent, or Firm*—Harness, Dickey & Pierce, P.L.C.

(57) ABSTRACT

A method for processing data is proposed, particularly image data in a medical system, in which a plurality of imaging modalities for capturing the data and their associated apparatus for locally processing and storing the data are connected to one another via a data transmission unit for the purpose of data interchange. Common data for all modalities are respectively stored locally and are coordinated with one another such that the respective modality remains active regardless of the state of the data transmission unit.

19 Claims, 2 Drawing Sheets

METHOD AND APPARATUS FOR PROCESSING DATA, AND MEDICAL APPLIANCE SYSTEM FOR PROCESSING DATA

The present application hereby claims priority under 35 U.S.C. §119 on German patent application number DE 10 2004 016 578.5 filed Mar. 31, 2004 and on U.S. provisional patent application Ser. No. 60/557,689 filed Mar. 31, 2004, the entire contents of both of which are hereby incorporated herein by reference.

FIELD OF THE INVENTION

The invention generally relates to a method and/or an apparatus for processing data, particularly image data, e.g. examination image data in a medical system. The invention also generally relates to a medical appliance system.

BACKGROUND OF THE INVENTION

The apparatus for processing data generally includes a plurality of "modalities". In this context, "modality" is understood to refer to a recording unit, e.g. an X-ray unit, a computer tomograph for capturing data, such as examination image data, which includes an apparatus for processing and locally storing (over a limited time) the data, i.e. the examination image data. For the purpose of interchanging the data, a plurality of modalities are connected to one another via a data transmission unit, e.g. a data bus system or a communication network, e.g. the "image communication network" based on the DICOM (Digital Imaging and Communications in Medicine) standard. The DICOM standard is an industrial standard for transmitting images and further medical information between computers in order to allow digital communication between diagnostic and therapeutic appliances from different manufacturers (=modalities).

The management and archiving of the data, e.g. of image data, parameters for medical appliances, system parameters for the modalities, are largely determined by the use of the respective computer system, particularly of the operating and file system for the respective modality.

In this context, the data are generally managed and archived using files. The use of files for data and parameter management has fundamental advantages over a database in terms of storage, data protection and organization using directories, which are based on operating system services and interfaces which are firstly distinguished by high performance and standard interfaces for access. They make it largely possible to achieve the greatest platform independence and to access well tested and reliable mechanisms.

In branched or networked systems with a plurality of modalities, it may be necessary to interchange data, particularly operating and system parameters, between a plurality of modalities or imaging medical systems, particularly to use or distribute the data jointly. This is normally done using files in network directories which are accessed by the individual modalities using the data transmission unit, e.g. a standard network. The services on which the standard network is based require an interruption-free network. That is to say that it is not possible to interrupt the network connection in the course of operation and to set it up again, since the result of this is that parameters can no longer be ascertained in the course of operation, or read operations which are in progress are terminated incorrectly only after long time overruns. For reasons of fail-safety in medical appliances, and the risk of data loss, this behavior is unacceptable. Furthermore, mobile modalities which are able to use common parameters can thus be implemented only to a limited extent.

SUMMARY OF THE INVENTION

An embodiment of the invention therefore includes an object of specifying a method for processing data, particularly image data in a medical system which includes a plurality of imaging modalities which are connected to one another in a particularly simple manner for the purpose of data interchange. It is also an aim of another embodiment, to specify a particularly suitable apparatus for processing data, and/or a medical appliance system.

In this case, an embodiment the invention is based on the consideration that common data representing all modalities, e.g. operating parameters, system parameters, bus parameters, should be made available to all modalities centrally. In so doing, the respective modality needs to be able to operate autarkically regardless of the state of the data transmission unit which connects the modalities. To this end, provision is made for a method of at least one embodiment for processing data for various imaging modalities to involve the data which represent all modalities, particularly system parameters, to be respectively stored locally and to be coordinated or aligned with one another such that the respective modality remains active regardless of the state of the data transmission unit.

To this end, one of the modalities is preferably defined as a master modality. To store the common data, the master modality is expediently allocated a master memory unit. The master memory unit is used to store system parameters, user data and/or image data, preferably as common data.

To align all modalities with current data largely simultaneously, the respective modality is provided with a replication unit which is used to synchronize the data, e.g. system parameters or image data, with the master modality. Depending on the type of data interchange and alignment, the data are aligned synchronously or asynchronously between the modalities, particularly between the master modality and the local other modalities, also called slave modalities.

If one of the common data items, particularly a system parameter, is now changed locally by one of the local modalities then a message about the change in the common data is preferably transmitted to the replication unit associated with the modality making the change. The relevant replication unit is then used to read the changed data and to transmit them to the master modality and to store them on the master modality in the master memory unit.

To align the data in the various modalities across networks, the master modality is used to allocate the changed data a time which determines the time of the change. The respective local modality expediently sends a change request to the master modality cyclically or else under event control, the time which is stored in the local modality and which is associated with the current common data being compared with the time which is stored in the master modality and which represents the time of the change. If the two times are not the same, the relevant modality is updated by transmitting the changed data with the more up-to-date or most recent change time. If the data are the same then there is no update.

With regard to the apparatus for processing data, this includes a plurality of imaging modalities for capturing the data and their associated apparatus for locally processing and storing the data, which are connected to one another via a data transmission unit for the purpose of data interchange, where common data representing all modalities are stored locally by virtue of the respective modality having an associated local memory unit and the common data are aligned by virtue of the respective modality having an associated replication unit which is used such that the respective modality remains active regardless of the state of the data transmission unit. In this case, the common data are aligned by virtue of the respective replication unit for one of the local modalities communicating with the master modality and its replication unit. In addition, the respective modality can be connected to a central image storage and image archiving unit via the data transmission unit. It is also possible for the respective modality to be connected to a central archive memory for the purpose of storing the locally captured image data centrally.

In one preferred application of at least one embodiment, the method is used in a medical appliance system. In this case, the medical appliance system for processing data, particularly image data, includes a plurality of imaging modalities for locally capturing the data and an apparatus, associated with the respective modality, for locally processing and storing the data, the modalities being connected to one another via a data transmission unit for the purpose of data interchange. In addition, for the purpose of autarkic operation of the local modalities and for the purpose of local storage of common data representing all modalities, the respective modality has an associated local memory unit, in which case and to align the common data for the respective modality there is a replication unit which is used such that the respective modality remains active regardless of the state of the data transmission unit.

In other words: data used jointly in all modalities, e.g. system parameters, are distributed over all participating appliances or modalities via a network using the above-described alignment method and the corresponding service, so that they are available to the respective modality locally in the file system. The alignment method operates totally independently of the other applications or systems implemented on the respective modality. The result of this is that the medical systems associated with a single modality can continue to access local parameters securely without being influenced by any network faults, but with the data being inherently synchronized with all other modalities or appliances in the network.

The advantages of an embodiment of the invention may include, in particular, that the alignment method takes place independently and autarkically on the respective modality. In particular, the alignment method takes place asynchronously or synchronously and separately from other systems of the modality and is also independent of network faults and failures. The respective modality thus always has all data available locally.

In addition, the alignment method uses the standard of the relevant operating or file system for the respective modality or target platform, which means that the alignment method can be tested particularly easily and quickly. This is very effective and inexpensive during development and allows a particularly simple product. To store the time of a data change (=timestamp), the timestamp from the file system is easily used, the result of which is that modalities can recognize changes even after several instances of turning on and off, without the need to operate and synchronize complex and specific data management. "Offline operation" of a mobile modality is thus possible without any problem. The changed data during the "offline operation" are updated in the manner described above after turning on again or reconnecting to the network.

BRIEF DESCRIPTION OF THE DRAWINGS

Example embodiments of the invention are explained in more detail with reference to the drawings, in which.

Parts which correspond to one another have been provided with the same reference symbols in all figures.

DETAILED DESCRIPTION OF THE EXAMPLE EMBODIMENTS

Figure 1:
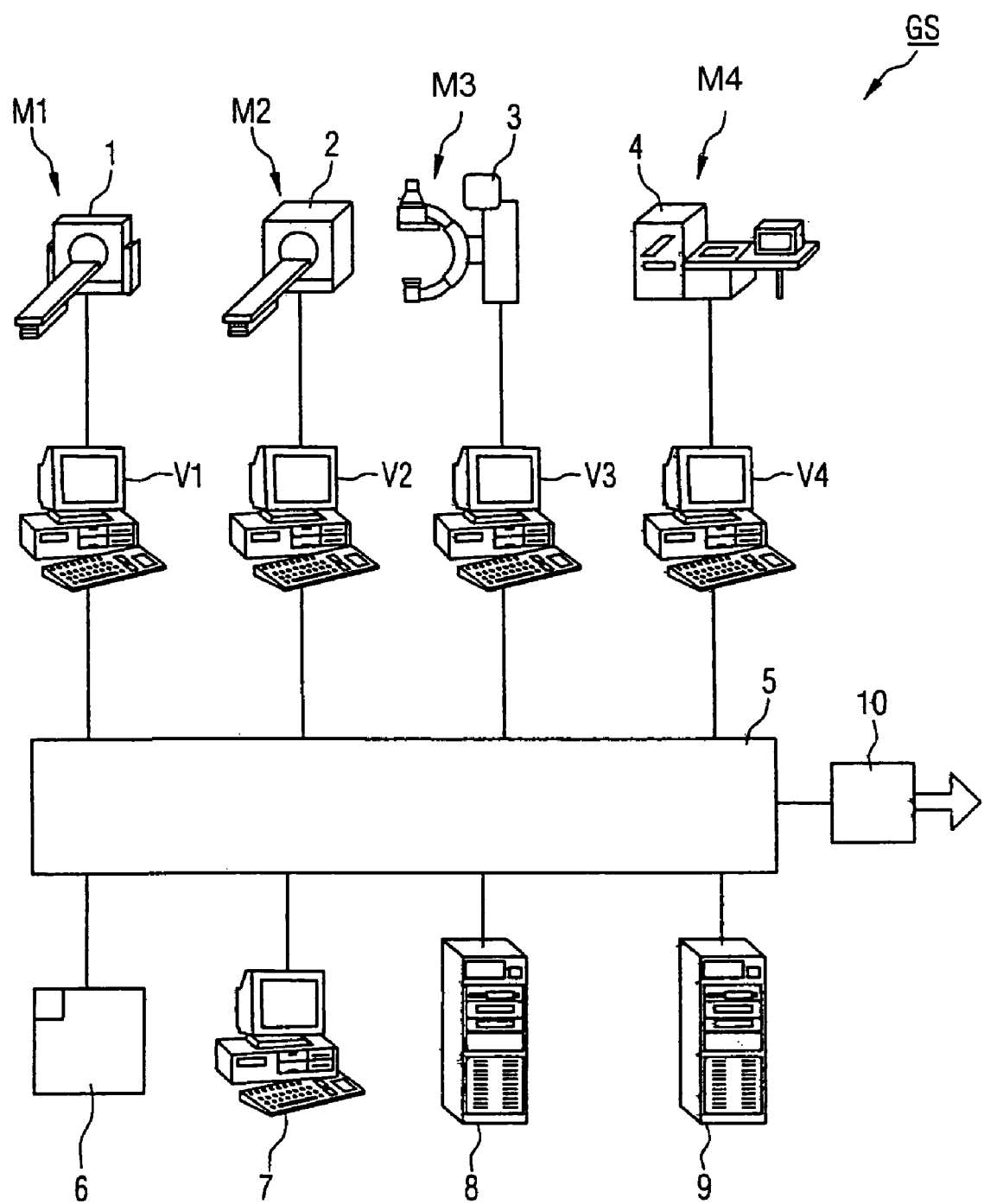
FIG. 1 schematically shows one possible embodiment of a medical appliance system having a plurality of modalities connected via a data transmission unit, and FIG. 2 schematically shows the flowchart for data alignment between the modalities.

FIG. 1 shows a medical appliance system GS in a "medical image communication network". The medical appliance system GS comprises a plurality of modalities M1 to M4 for capturing data, e.g. medical images. The modalities M1 to M4 are imaging appliances, for example, particularly a computer tomograph 1 for computer tomography, a magnetic resonance unit 2, a digital subtraction angiography unit 3 and an X-ray unit 4 for digital radiography. The respective modality M1 to M4 has an associated apparatus V1 to V4 for locally processing and storing the data. The apparatus V1 to V4 used is a computer or a workstation, for example, which can be used to process the captured data and to store them locally, particularly according to time limits. It is also possible to input patient data associated with the data.

The modalities M1 to M4 and their respective associated apparatus V1 to V4 are connected to one another via a data transmission unit 5. The data transmission unit 5 forms the image communication network and is in the form of a data bus system or in the form of a network, for example.

Connected to the data transmission unit 5 for the purpose of centrally processing and archiving the data there may be further appliances, e.g. a central image storage and image archiving unit 6, a central archive memory 7 as a findings console with a local image store, and/or further workstations 8 or servers 9, which are used as patient data servers or program servers.

In this case, images and data are interchanged via the data transmission unit 5 on the basis of the "DICOM standard", an industrial standard for transmitting images and data between modalities M1 to M4, i.e. medical diagnostic and therapeutic appliances from different manufacturers.

In addition, the data transmission unit 5 may have a network interface 10 connected to it, e.g. a modem or a radio interface, which connects the data transmission unit 5 to a global network, for example the Internet or World Wide Web.

Figure 2:
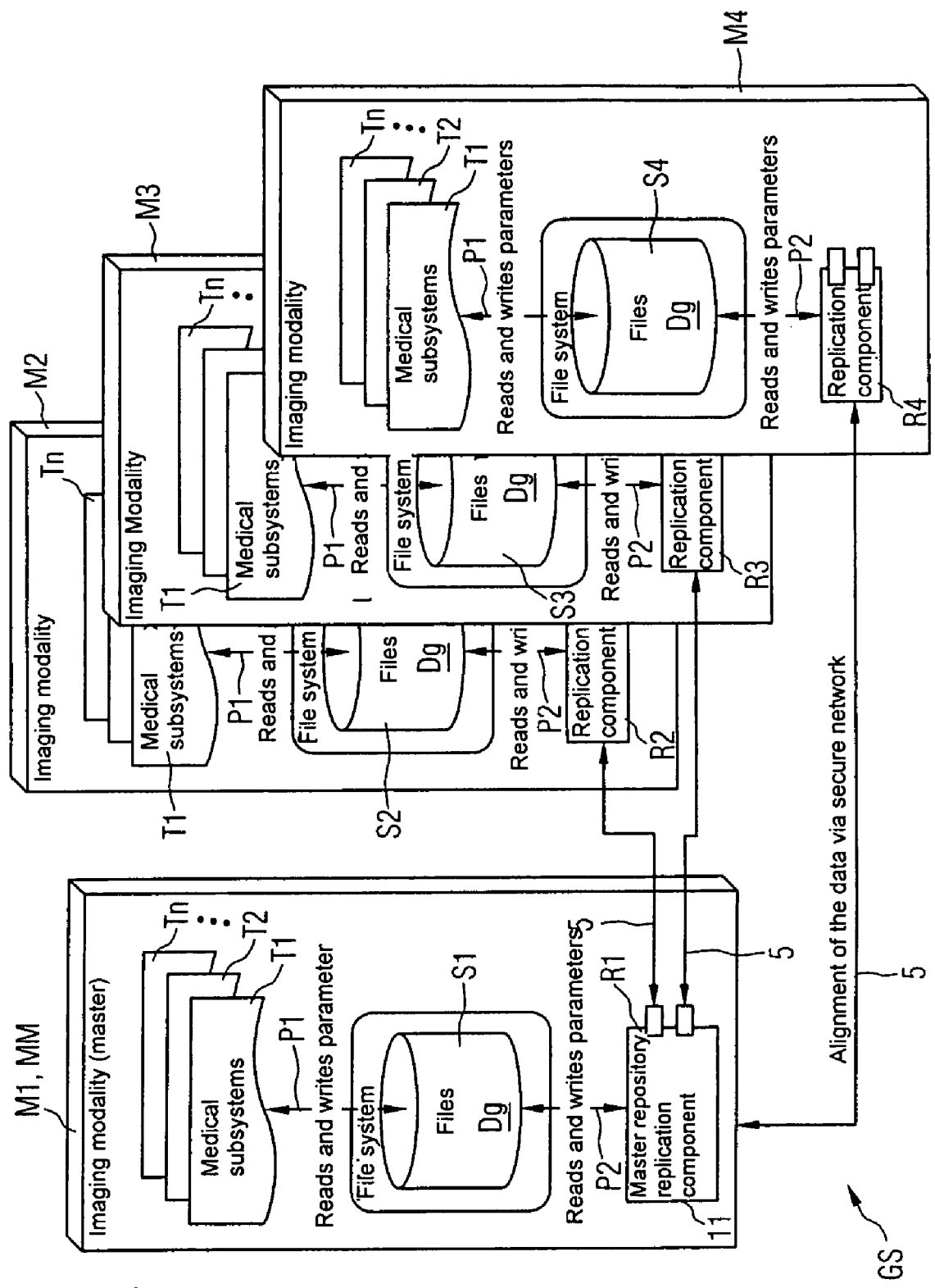

FIG. 2 schematically shows a flowchart for data alignment between the modalities M1 to M4.

In this case, the data alignment, the data Dg which are common to all modalities M1 to M4 are respectively stored locally. To this end, the respective modality M1 to M4 comprises an associated memory unit S1 to S4. Depending on the type and form of the medical appliance system GS, the memory unit S1 to S4 may alternatively or additionally be provided on the associated apparatus V1 to V4. In the exemplary embodiment described here, the memory unit S1 to S4 is arranged on the respective modality M1 to M4. The common data Dg, i.e. the common data Dg representing all modalities M1 to M4, which are stored are system parameters, appliance data, user data and/or image data, for example.

In this case, the common data Dg representing all modalities M1 to M4 are coordinated with one another, for secure operation, such that the respective modality M1 to M4 remains active regardless of the state of the data transmission unit 5. To this end, the respective modality M1 to M4 is provided with a replication unit R1 to R4 which is used to synchronize the common data Dg, e.g. system parameters or image data, with the other modalities M1 to M4. In particular, one of the modalities M1 is defined as a master modality MM, which is used to perform the alignment of the common data Dg in the event of a data change by one of the modalities M1 to M4.

Expediently, the master modality MM comprises a master memory unit 11 for storing the common data Dg. Depending on the type and design of the master modality MM, the memory unit 11 (also called master repository) may also be integrated in the relevant replication unit R1 or may be in the form of a separate module.

In detail, the alignment method involves the common data Dg being aligned synchronously or asynchronously between the modalities M1 to M4, particularly between the master modality MM and the local other modalities M2 to M4 (also called slave modalities). If one of the common data items Dg, particularly a system parameter, is changed locally by one of the local modalities M1, M2, M3 and/or M4, a message about the change in the common data Dg is transmitted to the replication unit R1 to R4 associated with the modality M1 to M4 making the change.

In this case, by way of example, a medical subsystem T1 to Tn associated with the respective modality M1 to M4 changes a system parameter by overwriting the common data Dg in the associated local memory unit S1 to S4, as indicated by the arrow P1. The changed common data Dg are then read from the memory unit S1 to S4 using the replication unit R1 to R4, as indicated by the arrow P2.

Next, the relevant replication unit R2 to R4 is used to read the changed common data Dg and to transmit them to the master modality MM via the data transmission unit 5, particularly via a secure connection. Since the modality M1 is defined as master modality MM, there is no need to transmit the changed common data Dg. Both if the replication unit R1 in the master modality MM is used to receive changed common data Dg from the other local modalities M2 to M4 and if the master modality MM itself stores changed common data Dg in the replication unit R1, the changed common data Dg are stored in the master memory unit 11.

In addition, the master modality MM is used to allocate the changed common data Dg a time which determines the time of the change. To align the common data Dg between the modalities M1 to M4, the respective local modality M2 to M4 sends a change request to the master modality MM cyclically, the time which is stored in the local modality M2 to M4 and which is associated with the current common data Dg being compared with the time which is stored in the master modality MM and which represents the time of the change. If the two times are not the same, the relevant modality M2 to M4 is then updated by transmitting the changed common data Dg with the most up-to-date or most recent change time to the modality.

In other words: the alignment method or the alignment service essentially includes a replication component or unit R1 to R4 whose system is independent of the subsystems T1 to Tn and/or of the other modalities M1 to M4, which exists on every modality M1 to M4 and which is connected to a modality M1, defined as master modality MM, having a master repository—the master memory unit 11—in order to synchronize the common data Dg. The master memory unit 11 is a local file system for the master modality MM.

Generally, the data alignment in the image communication network of a medical appliance system GS with a medical application takes place as follows:

When a modality M1 to M4 changes a parameter which is available in the network, it does so only locally in the file system for the local modality M1 to M4 and hence securely. Next, the modality M1 to M4 notifies the associated replication unit R1 to R4 about this change, also just using a secure and local communication path. This notification serves, in particular, as an event indication denoting that the parameter has changed, and no common data Dg are transmitted. As a result, there are also no power losses in the medical procedure. The replication unit R1 to R4 then reads the changed common data Dg from the file system, the memory unit S1 to S4, and attempts to transmit them to the master modality MM via a secure and encrypted network connection from the data transmission unit 5.

If the network connection is not possible, just a local note is made that the change has taken place and at what time, in order to be able to send it at a later time. If a change by the master modality MM is involved, then no communication takes place via the network, i.e. no data transmission is necessary.

The master modality MM receives the changed common data Dg when a network connection is possible, and enters it into the local file system associated with the master memory unit 11. The master modality MM thus has the change immediately available. The other modalities M2 to M4 do not have this change available until after it has been requested from the master modality MM and the changed common data Dg have subsequently been transmitted. In addition, the master modality MM notes the time of the last change.

The other modalities M2 to M4 use the associated replication unit R2 to R4 to check the master modality MM in the network cyclically to determine whether changes have taken place. In this case, they respectively send the time of their previous check. The master modality MM compares this time with the time of a change which has been received last and, if appropriate, responds with the new common data Dg, which are in turn immediately entered into the file system, into the memory units S2 to S4, on the checking modality M2 to M4. All other modalities M2 to M4 thus have current changes available too.

Alternatively, instead of the respective modality M2 to M4 enquiring with the master modality MM and changed common data Dg subsequently being transmitted to the enquiring modalities M2 to M4, provision may be made for common data Dg to be changed actively and with real-time capability on all modalities M1 to M4. Particularly in the case of smaller systems with fewer than 30 modalities M1 to Mn in an appliance system GS, there is active notification on the master modality MM in the direction of the other modalities M2 to Mn. This has the advantage that the other modalities M2 to Mn (slave modalities) do not first need to wait one cycle, but rather are updated immediately. This results in a high level of network traffic and a high level of power consumption on the master modality MM. For this reason, this solution is used only for smaller appliance systems GS.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of processing data in which a plurality of imaging modalities configured to capture the data, and associated apparatuses configured to locally process and store the data, are connected to one another via a data transmission unit, the data transmission unit configured to interchange data between the plurality of imaging modalities, the method comprising:
storing data common to the plurality of imaging modalities on each imaging modality, one of the plurality of imaging modalities being defined as a master imaging modality; and
coordinating the stored common data between the plurality of imaging modalities such that a respective imaging modality remains operational regardless of a state of the data transmission unit, wherein coordinating the stored common data includes:
transmitting a message by the imaging modality to a replication unit included in the imaging modality when the imaging modality makes a change in the common data stored therein,
reading and transmitting, by the replication unit, the changed common data to the master imaging modality,
storing, by the master imaging modality, the changed common data in a master memory unit of the master imaging modality,
allocating by the master imaging modality to the changed common data the time of change in the common data,
cyclically transmitting, by another imaging modality of the plurality of imaging modalities to the master imaging modality, a change request and the time associated with the common data currently stored in the another imaging modality,
comparing the time of change in the common data stored in the master imaging modality with the time transmitted by the another imaging modality, and
updating the common data stored in the another imaging modality with the common data stored in the master imaging modality when the time transmitted by the another imaging modality and the time stored in the master imaging modality are not the same.

2. The method as claimed in claim 1, wherein the stored common data includes at least one of system parameters, user data and image data.

3. The method as claimed in claim 1, further comprising:
synchronizing the common data with the master imaging modality using the replication unit.

4. The method as claimed in claim 3, further comprising:
synchronously or asynchronously aligning the common data between the plurality of imaging modalities.

5. The method as claimed in claim 3, further comprising:
synchronously or asynchronously aligning the common data between the master imaging modality and the other imaging modalities.

6. The method as claimed in claim 1, wherein the method is for processing image data in a medical system.

7. The method as claimed in claim 1, further comprising:
jointly using the stored common data for all the plurality of imaging modalities in each associated apparatus of each respective imaging modality of the plurality of imaging modalities.

8. The method as claimed in claim 7, wherein the common data stored includes system parameters.

9. An apparatus configured to process data in which a plurality of imaging modalities configured to capture the data, and apparatuses associated with the plurality of imaging modalities and configured to locally process and store the data, are connected to one another via a data transmission unit, the data transmission unit configured to interchange data between the plurality of imaging modalities, the apparatus comprising:
a plurality of local memory units associated with each imaging modality of the plurality of imaging modalities, the plurality of local memory units configured to locally store data common to the plurality imaging modalities on each imaging modality, one of the plurality of imaging modalities being defined as a master imaging modality; and
a plurality of replication units included in each imaging modality, the plurality of replication units configured to align the common data between the plurality of imaging modalities such that a respective imaging modality remains operational regardless of a state of the data transmission unit, wherein
at least one replication unit included in a respective imaging modality is configured to receive a message from the respective imaging modality regarding a change in the common data stored therein and to transmit the changed common data to the master imaging modality,
the master imaging modality is configured to store the changed common data and to allocate the stored common data a time indicating the change in the common data,
another imaging modality of the plurality of imaging modalities is configured to cyclically transmit a change request and the time associated with the common data stored therein to the master imaging modality, and
the master imaging modality is further configured to compare the time transmitted by the another imaging modality with the time allocated to the stored common data and to update the common data stored in the another imaging modality with the common data stored in the master imaging modality when the time transmitted by the another imaging modality and the time allocated to the common data stored in the master imaging modality are not the same.

10. The apparatus as claimed in claim 9, wherein the master imaging modality includes a master memory unit configured to store the common data.

11. The apparatus as claimed in claim 9, wherein the at least one replication unit included in the respective imaging modality communicates with the master imaging modality and its associated replication unit in order to align the common data.

12. The apparatus as claimed in claim 9, wherein the respective imaging modality is connected to a central image storage and image archiving unit via the data transmission unit.

13. The apparatus as claimed in claim 9, wherein the respective imaging modality is connected to a central archive memory via the data transmission unit.

14. The apparatus as claimed in claim 9, wherein the apparatus processes image data in a medical system.

15. A medical appliance system configured to process data, the medical appliance system including a plurality of imaging modalities configured to capture the data, and apparatuses associated with the plurality of imaging modalities and configured to locally process and store the data, the plurality of imaging modalities connected to one another via a data transmission unit configured to interchange data between the plurality of imaging modalities, wherein common data representing the plurality of imaging modalities are locally stored in a respective local memory unit of each imaging modality; and the common data of each imaging modality are aligned by a replication unit included in each imaging modality such that the imaging modality remains operational regardless of a state of the data transmission unit, wherein the replication unit is configured to receive a message from the imaging modality regarding a change in the common data stored therein and to transmit the changed common data to an imaging modality of the plurality of imaging modalities defined as a master imaging modality, the master imaging modality is configured to store the changed common data and to allocate the stored common data a time indicating the change in the common data, another imaging modality of the plurality of imaging modalities is configured to cyclically transmit a change request and the time associated with the common data stored therein to the master imaging modality, and the master imaging modality is further configured to compare the time transmitted by the another imaging modality with the time allocated to the stored common data and to update the common data stored in the another imaging modality with the common data stored in the master imaging modality when the time transmitted by the another imaging modality and the time allocated to the common data stored in the master imaging modality are not the same.

16. The system as claimed in claim 15, wherein the medical appliance system processes image data in a medical system.

17. A method of processing data, comprising:

connecting a plurality of imaging modalities configured to capture the data, and a plurality of, associated with the plurality of imaging modalities and configured to locally process and store the captured data, to one another via a data transmission unit configured for data interchange, wherein data common to the plurality of imaging modalities are stored on each imaging modality and the stored common data are coordinated with one another such that a respective imaging modality remains operational regardless of a state of the data transmission unit, wherein one imaging modality of the plurality of imaging modalities is defined as a master imaging modality and coordinating the stored common data includes transmitting a message regarding a change in the common data stored in an imaging modality to a replication unit included therein, reading and transmitting, by the replication unit, the changed common data to the master imaging modality, storing, by the master imaging modality, the changed common data in a master memory unit of the master imaging modality, allocating, by the master imaging modality to the changed common data, the time of change in the common data, cyclically transmitting, by another imaging modality of the plurality of imaging modalities to the master imaging modality, a change request and the time associated with the common data currently stored in the another imaging modality, comparing the time of change allocated to the common data stored in the master imaging modality with the time transmitted by the another imaging modality, and updating the common data stored in the another imaging modality with the common data stored in the master imaging modality when the time transmitted by the another imaging modality and the time allocated to the common data stored in the master imaging modality are not the same.

18. The method as claimed in claim 17, further comprising:

jointly using the stored common data for all the plurality of imaging modalities in each associated apparatus of each respective imaging modality of the plurality of imaging modalities.

19. The method as claimed in claim 18, wherein the common data stored includes system parameters.

* * * * *